United States Patent
Roura Fernandez et al.

(10) Patent No.: US 12,048,794 B2
(45) Date of Patent: Jul. 30, 2024

(54) DEVICE FOR THERAPEUTIC PLASMA EXCHANGE

(71) Applicant: GRIFOLS WORLDWIDE OPERATIONS LIMITED, Dublin (IE)

(72) Inventors: Carlos Roura Fernandez, Sant Cugat del Valles (ES); Carlos Roura Salietti, Sant Cugat del Valles (ES); Antonio Manuel Paez Regadera, Sant Cugat del Valles (ES)

(73) Assignee: GRIFOLS WORLDWIDE OPERATIONS LIMITED, Dublin (IE)

( * ) Notice: Subject to any disclaimer, the term of this patent is extended or adjusted under 35 U.S.C. 154(b) by 476 days.

(21) Appl. No.: 15/926,222

(22) Filed: Mar. 20, 2018

(65) Prior Publication Data
US 2018/0280603 A1    Oct. 4, 2018

(30) Foreign Application Priority Data
Mar. 30, 2017   (ES) .................................. 201700336

(51) Int. Cl.
*A61M 1/34*   (2006.01)
*A61M 1/16*   (2006.01)
(Continued)

(52) U.S. Cl.
CPC ........ *A61M 1/3496* (2013.01); *A61M 1/1603* (2014.02); *A61M 1/1621* (2014.02);
(Continued)

(58) Field of Classification Search
CPC .... A61M 1/3621; A61M 1/34; A61M 1/1603; A61M 1/1621; A61M 1/30; A61M 1/342;
(Continued)

(56) References Cited

U.S. PATENT DOCUMENTS

| 4,954,128 A | * | 9/1990 | Ford ....................... A61M 1/30 604/6.05 |
| 5,207,642 A | | 5/1993 | Orkin et al. |

(Continued)

FOREIGN PATENT DOCUMENTS

| CA | 2 650 595 C | 10/2016 |
| CN | 100998898 A | 7/2007 |

(Continued)

OTHER PUBLICATIONS

Flanigan, The composition of dialysis fluid, 2000, p. 1-7 (Year: 2000).*

(Continued)

*Primary Examiner* — Hayden Brewster
(74) *Attorney, Agent, or Firm* — Knobbe, Martens, Olson & Bear LLP

(57) ABSTRACT

A device for therapeutic plasma exchange includes an extracorporeal circuit, which includes a blood supply line, a separating unit, a line for infusion of formed elements, a line for infusion of replacement fluid, a blood plasma line, an anticoagulant line and at least one independent line for therapeutic drugs. The independent line can include a storage for the therapeutic drug, a conveyer of therapeutic drug, a propelling device and a controller configured to control flow of the therapeutic drug.

11 Claims, 3 Drawing Sheets

(51) Int. Cl.
  *A61M 1/30* (2006.01)
  *A61M 1/36* (2006.01)
  *A61M 5/168* (2006.01)

(52) U.S. Cl.
  CPC .............. *A61M 1/30* (2013.01); *A61M 1/342* (2013.01); *A61M 1/3672* (2013.01); *A61M 5/16827* (2013.01); *A61M 2202/0014* (2013.01); *A61M 2202/0415* (2013.01); *A61M 2205/3334* (2013.01)

(58) Field of Classification Search
  CPC .............. A61M 1/3496; A61M 1/3626; A61M 1/3633; A61M 1/3672; A61M 5/16827; A61M 2202/0014; A61M 2202/0415; A61M 2205/3334; A61M 1/3403; A61M 1/3434; A61M 1/3437; A61M 1/16; A61M 1/341; A61M 1/3441; A61M 1/3455; A61M 1/3458; A61M 1/3472; A61M 1/3482; A61M 1/3609; A61M 1/3675; A61M 2205/15; A61M 2205/3306; A61M 2205/3368; A61M 1/14; A61M 1/1605; A61M 1/1613; A61M 1/1615; A61M 1/1647; A61M 1/165; A61M 1/1656; A61M 1/166; A61M 1/1664; A61M 1/1666; A61M 1/1668; A61M 1/167; A61M 1/1696; A61M 1/303; A61M 1/308; A61M 1/3406; A61M 1/3413; A61M 1/3427; A61M 1/3431; A61M 1/3444; A61M 1/3448; A61M 1/3468; A61M 1/3475; A61M 1/3479; A61M 1/3493; A61M 1/3603; A61M 1/3607; A61M 1/3635; A61M 1/3653; A61M 1/3656; A61M 1/3658; A61M 2202/0486; A61M 2205/058; A61M 2205/3317; A61M 2205/3331; A61M 2205/3341; A61M 2205/3351; A61M 2205/3355; A61M 2205/3365; A61M 2205/3393; A61M 2205/36; A61M 2205/502; A61M 2205/702; A61M 2209/084; A61M 60/279; A61M 60/50; A61K 2300/00; A61K 31/191; A61K 31/194; A61K 31/7004; A61K 33/06; A61K 33/10; A61K 33/14; A61K 33/20; A61K 33/42; A61K 35/16; A61K 35/14; A61K 9/0019; A61P 7/00; A61P 7/08; A61P 3/00; A61P 3/06; A61P 9/00; B01D 61/145; B01D 2313/40; B01D 2315/06; B01D 61/00; B01D 61/002; B01D 61/142; B01D 61/243; B01D 63/046; B01D 69/12; B01D 69/144; A01K 63/04; A01K 63/042; B03D 1/1418; B03D 1/1487; B03D 1/247; B04B 5/02; C02F 1/24; C02F 2101/16; C02F 2101/163; C02F 2101/166; F04B 43/0072; F04B 43/0081; F04B 43/1253; G01N 27/221; G01N 27/228; G01N 33/48707
  See application file for complete search history.

(56) References Cited

U.S. PATENT DOCUMENTS

| | | |
|---|---|---|
| 5,679,245 A | 10/1997 | Manica |
| 5,698,090 A | 12/1997 | Bene et al. |
| 6,808,503 B2 * | 10/2004 | Farrell ............... A61M 1/3675 210/252 |
| 9,199,022 B2 | 12/2015 | Fulkerson |
| 2008/0015487 A1 * | 1/2008 | Szamosfalvi ....... A61M 1/3658 604/6.07 |
| 2009/0084717 A1 * | 4/2009 | Delmage ............. A61M 1/3403 210/201 |
| 2010/0252490 A1 * | 10/2010 | Fulkerson ........... A61M 1/1664 210/96.2 |
| 2012/0022423 A1 * | 1/2012 | Sternby ............... A61K 31/194 604/6.07 |
| 2015/0165109 A1 * | 6/2015 | Fischer ............... A61M 1/3431 210/141 |
| 2016/0051746 A1 * | 2/2016 | Case ................... A61M 1/3672 210/85 |
| 2017/0065762 A1 * | 3/2017 | Larsen ............... A61M 1/3468 |
| 2017/0258979 A1 * | 9/2017 | Fulkerson ........... A61M 1/1086 |
| 2017/0296727 A1 * | 10/2017 | Burbank ............. A61M 1/3403 |
| 2018/0071450 A1 * | 3/2018 | Ruhland ........... A61M 5/16804 |
| 2018/0318348 A1 * | 11/2018 | Corash ................ A61K 35/16 |

FOREIGN PATENT DOCUMENTS

| | | | |
|---|---|---|---|
| EP | 0171749 A1 | 2/1986 | |
| EP | 1101502 A2 | 5/2001 | |
| ES | 2255772 A1 * | 7/2006 | |
| ES | 2255772 B1 | 9/2007 | |
| JP | 63-102763 A | 5/1988 | |
| JP | 5-508560 A | 12/1993 | |
| JP | 2013-509924 A | 3/2013 | |
| JP | 2013-248336 A | 12/2013 | |
| RU | 2271834 C1 | 3/2006 | |
| RU | 2174412 C2 | 10/2011 | |
| WO | 91/15253 A2 | 10/1991 | |
| WO | 97/05938 A1 | 2/1997 | |
| WO | WO 03/049775 A2 | 6/2003 | |
| WO | WO-2004082731 A2 * | 9/2004 | ............ A61M 1/30 |
| WO | 2011/054693 A1 | 5/2011 | |
| WO | 2016/057982 A1 | 4/2016 | |

OTHER PUBLICATIONS

Office Action in corresponding Japanese Patent Application No. 2018-043808 dated Dec. 13, 2019, 8 pages.

International Search Report of corresponding Spanish Patent Application No. 201700336—5 pages (Mar. 30, 2017).

Extended European Search Report of corresponding Patent Application No. 18163175.5—7 pages (Jul. 26, 2018).

Notification Regarding Defects dated Jan. 17, 2021 received in Israel Patent Application No. 258015.

Search Report dated May 13, 2021 in Russian Application No. 2018109409/14(014500).

Office Action dated May 13, 2021 in Russian Application No. 2018109409/14(014500).

Examination Report mailed Jan. 24, 2022 in Indian Application No. 201844008874.

\* cited by examiner

DEVICE FOR THERAPEUTIC PLASMA EXCHANGE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

The present disclosure relates to the field of medical devices, and relates in particular to a device for therapeutic plasma exchange that allows the administration of a therapeutic drug simultaneously with the execution of the plasma exchange procedure and independently of the administration of a replacement fluid.

Therapeutic plasma exchange (TPE) forms part of a larger group of techniques called plasmapheresis. In plasmapheresis, blood is withdrawn from the human body and is processed in such a way that the plasma is separated from the main formed elements of the blood (erythrocytes, leukocytes, platelets, among others). At present, plasmapheresis is used for a variety of reasons, including transfusion, donation of plasma for subsequent fractionation and obtaining blood derivatives, or the treatment of diseases, which are treated by removing factors specific to the disease from the blood plasma.

TPE is a particular type of plasmapheresis indicated as treatment in many diseases, in which the plasma that has been separated from the rest of the formed elements is discarded with the aim of removing the harmful substances from the patient's blood. The formed elements that have been separated are usually mixed with a liquid, known as replacement fluid, and returned to the patient. The commonest replacement fluids include isotonic saline solutions, colloidal solutions of albumin, or fresh plasma, among others. To avoid hypotension or peripheral oedema, it is preferable to supply a replacement fluid based on a colloidal solution of albumin or fresh plasma capable of maintaining the oncotic pressure. In most cases albumin at 4-5% in isotonic saline solution is the preferred option as replacement fluid, because in contrast to fresh plasma, it is not specific to a particular blood group and presents less risk of allergic reactions.

One of the main risks arising from the use of the TPE technique is due to the decrease in the concentration of most of the plasma proteins, such as clotting factors, transport proteins, proteins of the complement system, as well as antibodies, and in particular immunoglobulins G. For this reason, it is often necessary to administer therapeutic drugs after completing the plasma exchange procedure, with the aim, among others, of rebalancing the normal levels of the plasma proteins in the patient. Said administration is usually by the intravenous, intramuscular or subcutaneous route, among others.

There is a need for TPE devices that allow one or more therapeutic drugs to be administered simultaneously with execution of the plasma exchange procedure, in such a way that makes it possible, among other things, to maintain the patient's levels of plasma proteins during the time that the plasma exchange procedure takes, without having to wait for it to end to be rebalanced.

The TPE devices known in the prior art only allow a therapeutic drug to be administered if it is dissolved in the replacement fluid. This involves various problems and their consequent risks to the patient's health, among them the risk of manipulation of the replacement fluid or the impossibility of controlling the flow rate of the therapeutic drug independently of the flow rate of the replacement fluid, among others.

Devices for plasmapheresis or plasma exchange are known in the prior art. For example, U.S. Pat. No. 5,679,245A discloses an apparatus for extracorporeal treatment of blood that comprises a filtration unit, a primary circuit and a secondary circuit. Said patent also discloses an anticoagulant fluid line and a replacement fluid line, which converge on the primary circuit.

Another drawback of the TPE devices known in the prior art is their large size and difficult portability, meaning that the patient has to go to the medical centre to receive treatment. There is therefore a need for TPE devices that overcome the drawbacks of the devices of the prior art.

SUMMARY

The inventors of the present invention have developed a TPE device that overcomes the aforementioned problems, and is surprising for several reasons. Among them, we may mention: the possibility of administering a therapeutic drug simultaneously with the plasma exchange procedure and independently of the administration of a replacement fluid, as well as improved portability.

In the present document, the term extracorporeal circuit refers to the combination of the various independent lines of the TPE device.

In the present document, the term line or independent line refers to the combination of structural elements selected from: liquid conveying means, liquid propelling means, liquid flow controlling means, liquid storage means, among others, which jointly perform a particular function in the TPE device. The term line does not refer to a minimum combination of structural elements, for example, in some cases a line may be made up of conveying means and storage means, while in other cases a line may be made up of conveying means, storage means, propelling means, among others. Moreover, several lines may share one or more structural elements. Examples of lines are:

Blood supply line or supply line: refers to the combination of structural elements that allows the patient's blood to be conveyed from the zone of withdrawal to the inlet of the separating unit.

Line for infusion of formed elements or formed elements line: refers to the combination of structural elements that allows the formed elements to be conveyed from the outlet of the separating unit to the infusion zone.

Line for infusion of replacement fluid or replacement fluid line: refers to the combination of structural elements that allows the replacement fluid to be conveyed from the replacement fluid container to the infusion zone.

Blood plasma line or plasma line: refers to the combination of structural elements that allows the blood plasma to be conveyed from the plasma outlet of the separating unit to the blood plasma container.

Anticoagulant line: refers to the combination of structural elements that allows the anticoagulant fluid to be conveyed from the anticoagulant fluid container to the supply line.

Line for infusion of therapeutic drug or line for therapeutic drug: refers to the combination of structural elements that allows the therapeutic drug to be conveyed from the therapeutic drug container to the infusion zone.

In the present document, the terms liquid conveying means or conveying means relate to elements such as tubes, lines, pipes, among others, that allow liquid to be conveyed between two points through their internal channel.

The terms liquid propelling means or propelling means refer to any element capable of transferring energy to a liquid to achieve movement thereof through the conveying means. In embodiments of the present invention, said propelling means are preferably pumps and more preferably peristaltic pumps.

The terms liquid flow controlling means or flow controlling means refer to any element capable of preventing/ allowing or regulating the passage of liquid through the conveying means. In embodiments of the present invention, said flow controlling means are preferably valves and/or peristaltic pumps.

It will be obvious to a person skilled in the art that one and the same element may sometimes perform the functions of propelling means and flow controlling means, for example a peristaltic pump may perform both functions. It will also be obvious to a person skilled in the art that the propelling means and the flow controlling means may be controlled electronically by a centralized control unit.

The terms liquid storage means, storage means or container are used synonymously in embodiments of the present invention to refer to any element that allows liquid to be contained within it and to be connected to a conveying means. Said storage means are preferably: bottles, vials, plastic bags, among others, or combinations thereof. It will be obvious to a person skilled in the art that the storage means may have an outlet and/or an inlet, depending on the function that they perform in the extracorporeal circuit. It will also be obvious to a person skilled in the art that the inlet and/or outlet of said storage means may be controlled by flow controlling means.

The term therapeutic drug refers to any therapeutic liquid known by a person skilled in the art. Preferably, said therapeutic drug comprises human plasma proteins selected from the group comprising albumin (5-25%), α-1-antitrypsin, von Willebrand factor, clotting factors such as factor VII, factor VIII and factor IX, immunoglobulins, plasminogen, plasmin, antithrombin III, fibrinogen, fibrin, thrombin or combinations thereof.

The term blood relates to whole blood, i.e. blood that contains all the formed elements of the blood such as erythrocytes, leukocytes, platelets, etc., in addition to plasma.

The term blood plasma or plasma refers to the acellular liquid part of the blood.

The term separating unit refers to any device capable of separating the blood into its corresponding cellular and acellular fractions. In the present document, said fractions are also called formed elements and plasma, respectively.

Thus, an aspect of the present invention discloses a TPE device that comprises an extracorporeal circuit that comprises a blood supply line, a separating unit, a line for infusion of formed elements, a line for infusion of replacement fluid, a blood plasma line, an anticoagulant line in addition to at least one independent line for therapeutic drugs.

Said independent line for therapeutic drugs comprises at least one therapeutic drug container, conveying means, propelling means and flow controlling means of said therapeutic drug. Preferably, said propelling means of said independent line for therapeutic drugs are at least one peristaltic pump, more preferably said peristaltic pump is a reversible peristaltic pump.

In another aspect of the present invention, the inventors have simplified a TPE device that comprises at least one line for therapeutic drugs, with which it is possible to obtain a portable TPE device that comprises at least one line for therapeutic drugs. Said simplification of the device has been achieved by the sharing of structural elements (conveying means, propelling means, flow controlling means, among others) by several of the lines known in the prior art (replacement fluid line, formed elements line, supply line, among others) in addition to the at least one line for therapeutic drugs.

In one embodiment, the line for therapeutic drugs of the device of the present invention shares structural elements with one or more of the other lines of the device. Preferably, said shared structural elements are the conveying means, the propelling means and the flow controlling means. In a preferred embodiment, said shared propelling means are at least one reversible peristaltic pump. In another preferred embodiment said shared flow controlling means are a radial distributor.

The term radial distributor refers to a type of distributor such as that disclosed in Spanish Patent ES 2255772 B1 (Grifols Lucas, V.). Said distributor has several lines that communicate with a common central point of the distributor and that may be put in communication with one another by the operation of the flow controlling means integrated in said radial distributor. Said operation may be controlled automatically by a centralized control unit.

In embodiments, the device of the present invention has a zone of withdrawal of the patient's blood and a zone of infusion to the patient, said zones are also called simply withdrawal zone and infusion zone. In some embodiments of the present invention, the withdrawal zone and the infusion zone are not coinciding zones of the device, while in other embodiments the withdrawal zone and the infusion zone are coinciding zones of the device.

In one embodiment of the present invention, the separating unit is a filter. In a preferred embodiment said filter is a hollow-fibre filter.

In one embodiment of the present invention, the line for infusion of formed elements, the line for infusion of replacement fluid and the line for therapeutic drugs comprise a bubble detector suitable for sending a signal capable of stopping the action of the propelling means when there is an air bubble in the conveying means of any of said lines.

In one embodiment of the present invention, the TPE device comprises means for measuring the pressure in the lines.

In one embodiment of the present invention, the TPE device comprises conveying means that allow communication between the replacement fluid line and the anticoagulant fluid line.

In one embodiment of the present invention the replacement fluid is an aqueous NaCl solution with a concentration of 0.8 to 1% w/v.

BRIEF DESCRIPTION OF THE DRAWINGS

Embodiments of the present invention is described in detail below in relation to the following figures, which do not limit the scope of the present invention, in which.

DETAILED DESCRIPTION OF EMBODIMENTS

Figure 1:
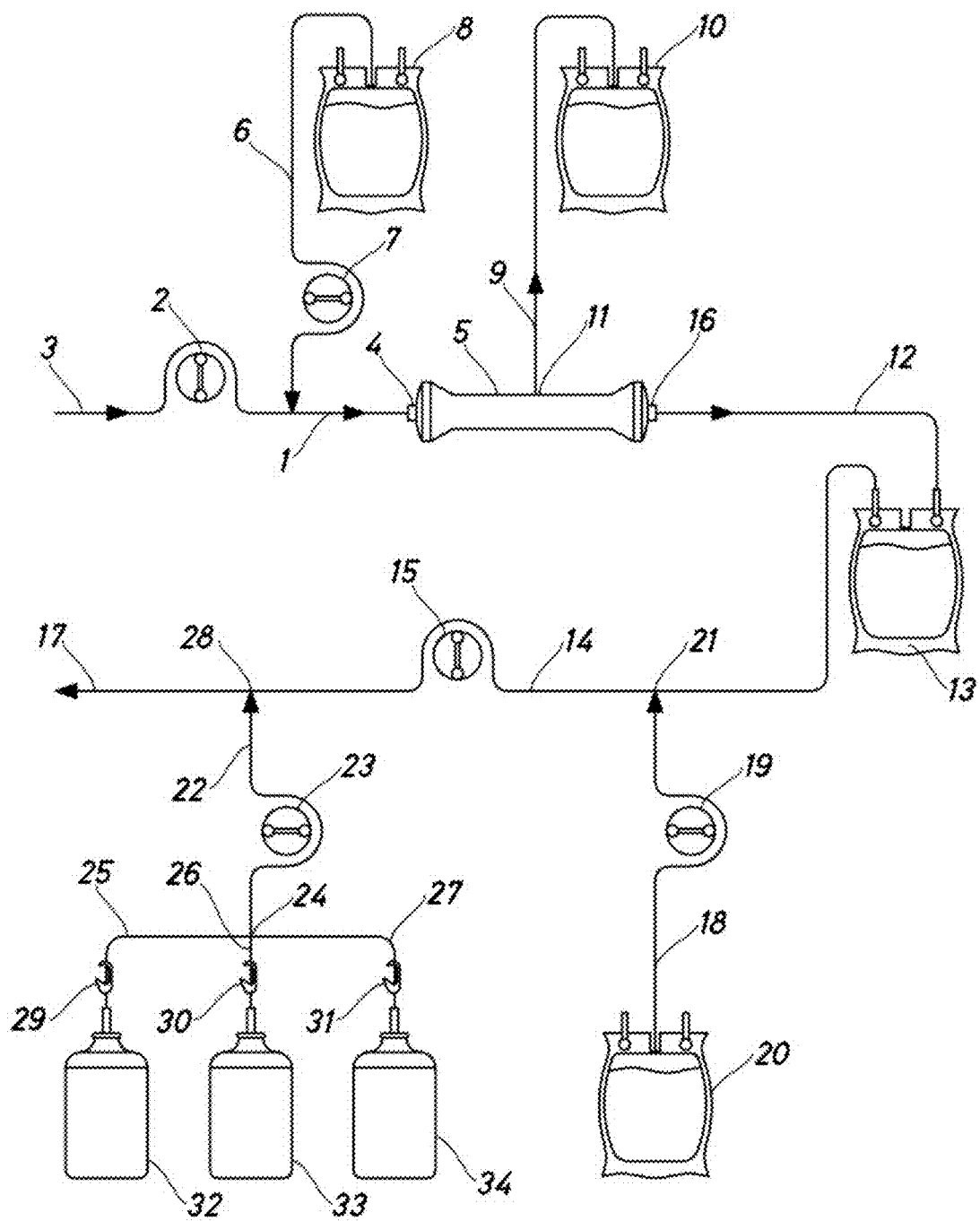
FIG. 1 is a diagram of a first embodiment of the TPE device according to an embodiment of the present invention.

In a first embodiment, as can be seen in FIG. 1, the TPE device contains a supply line made up of the tube -1- and the pump -2-. Said supply line extends from the withdrawal zone -3- to the inlet -4- of the separating unit -5- and transports whole blood from zone -3- to the inlet -4- of said separating unit. The anticoagulant line is made up of the tube -6-, the pump -7- and the bag -8- of anticoagulant, said anticoagulant line extends from the bag -8- to the supply line and transports anticoagulant fluid from said bag -8- to the supply line, where it is mixed with whole blood before the blood enters the separating unit -5-, where the patient's blood is separated into blood plasma and formed elements. The plasma line is made up of the tube -9- and the bag -10-, said plasma line extends from the outlet -11- of the separating unit to the bag -10- of blood plasma and transports said plasma from the outlet -11- to the bag -10-, where it is stored. The line for infusion of formed elements is made up of the tube -12-, the bag -13- of formed elements, the tube -14- and the pump -15-, said formed elements line extends from the outlet -16- of the separating unit to the infusion zone -17- and transports the formed elements separated by the unit -5- from the outlet -16- to the bag -13-, where they are stored in an initial step of the plasma exchange process, and then transports the formed elements stored in the bag -13- from said bag -13- to zone -17-. The line for infusion of replacement fluid is made up of the tube -18-, the pump -19-, the bag -20- of replacement fluid, the tube that extends from the junction point -21- to zone -17- and the pump -15-, said replacement fluid line extends from the bag -20- to zone -17- and transports replacement fluid from said bag -20- to zone -17-. Finally, the line for therapeutic drugs is made up of the tube -22-, the pump -23-, the tubes -25-, -26- and -27- that converge at the junction point -24- with the tube -22-, the valves -29-, -30- and -31- that regulate the passage of the therapeutic drugs from the vials -32-, -33- and -34- and the tube that extends from the junction point -28- to zone -17-, therefore the line for therapeutic drugs extends from the vials -32-, -33- and -34- to zone -17-. Said line for therapeutic drugs transports the therapeutic drugs from said vials -32-, -33- and -34- to the infusion zone -17-.

Figure 2:
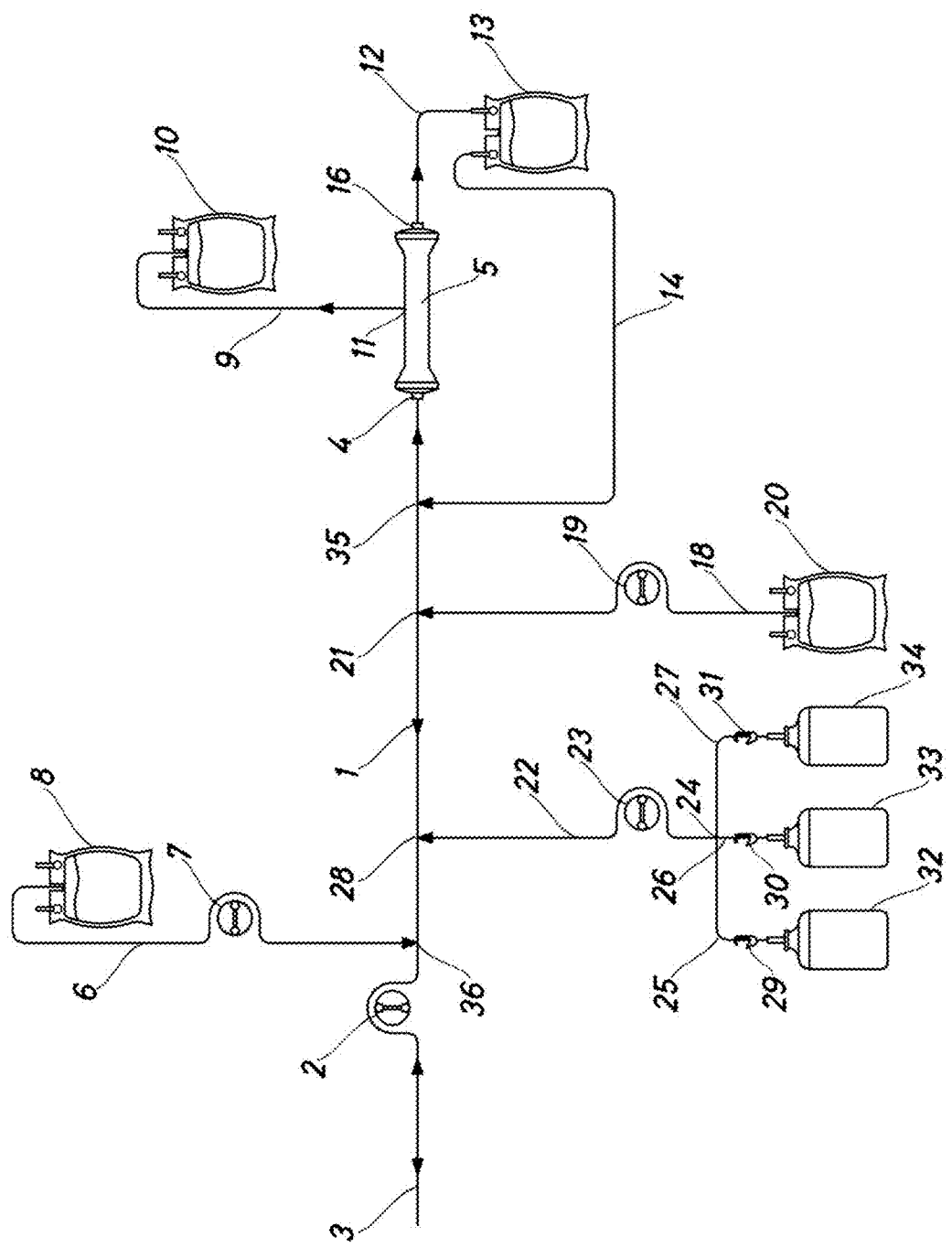
FIG. 2 is a diagram of a second embodiment of the TPE device according to an embodiment of the present invention.

In a second embodiment, as can be seen in FIG. 2, the TPE device contains a withdrawal zone coincident with an infusion zone, said zone -3- is called withdrawal/infusion zone. The TPE device additionally contains a supply line made up of the tube -1- and the pump -2-, said supply line extends from zone -3- to the inlet -4- of the separating unit -5- and transports whole blood from zone -3- to the separating unit -5-. The anticoagulant line is made up of the tube -6-, the pump -7- and the bag -8- of anticoagulant, said anticoagulant line extends from the bag -8- to the junction point -36- and transports anticoagulant fluid from the bag -8- to the supply line, where it is mixed with the whole blood before said blood enters the separating unit, where the blood is separated into blood plasma and formed elements. The plasma line is made up of the tube -9- and the bag -10- of plasma, said plasma line extends from the outlet -11- of the separating unit to the bag -10- and transports the blood plasma separated by the separating unit from the outlet -11- to the bag -10-, where it is stored. The line for infusion of formed elements is made up of the tube -12-, the bag -13- of formed elements, the tube -14-, the tube that extends from the junction point -35- to zone -3- and the pump -2-, therefore said formed elements line extends from the outlet -16- of the separating unit to zone -3- and transports the formed elements separated by the separating unit from the outlet -16- to zone -3-. The line for infusion of replacement fluid is made up of the tube -18-, the pump -19-, the bag -20- of replacement fluid, the tube that extends from the junction point -21- to zone -3- and the pump -2-, therefore said replacement fluid line extends from the bag -20- to zone -3- and transports replacement fluid from said bag -20- to zone -3-. Finally, the line for therapeutic drugs is made up of the tube -22-, the pump -23-, the tubes -25-, -26- and -27- that converge at the junction point -24- with the tube -22-, the valves -29-, -30- and -31- that regulate the passage of the therapeutic drugs from the vials -32-, -33- and -34-, the tube that extends from the junction point -28- to zone -3- and the pump -2-, therefore the line for therapeutic drugs extends from the vials -32-, -33- and -34- to zone -3-, transporting the therapeutic drugs from said vials to the infusion zone -3-.

Figure 3:
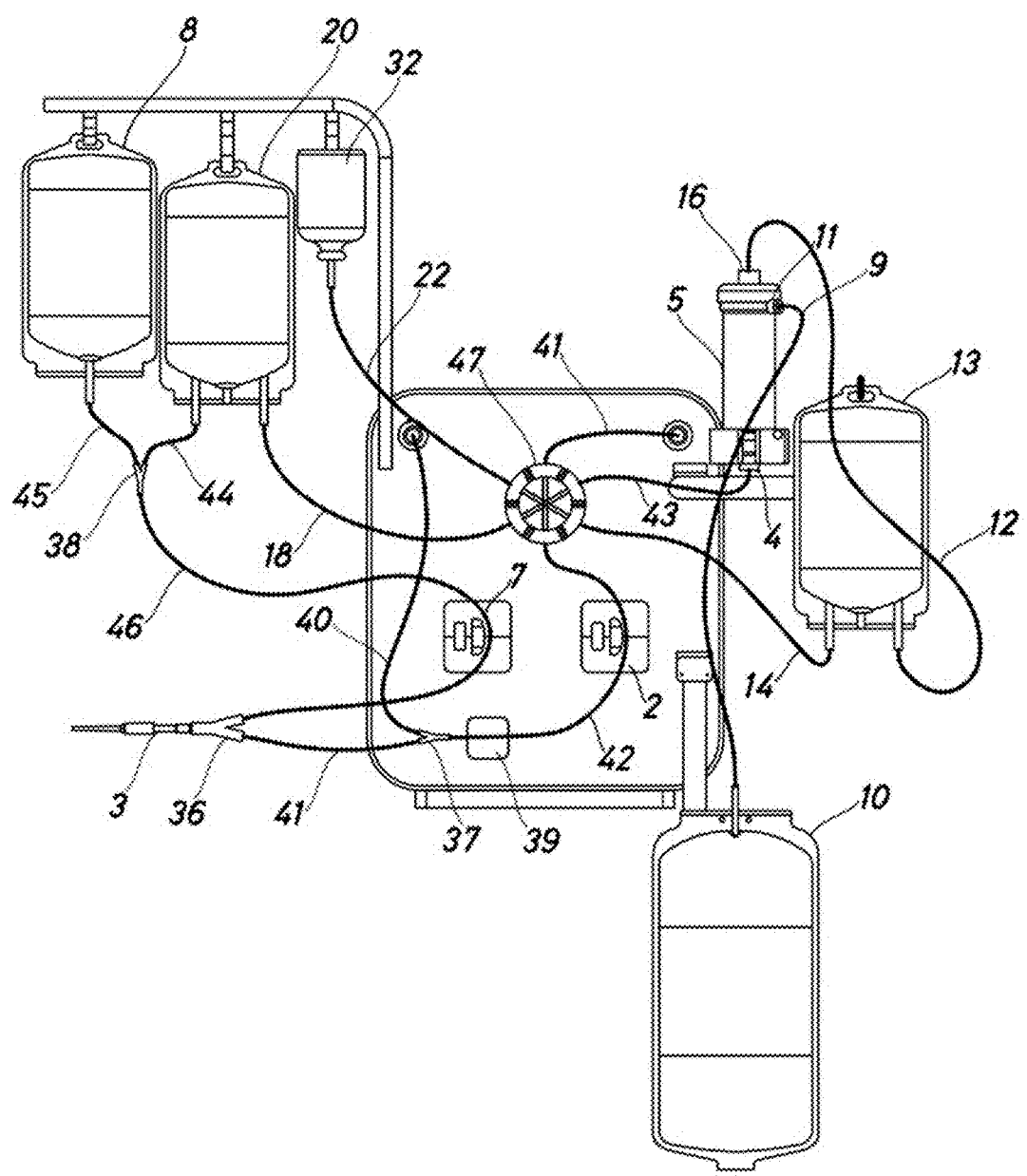
FIG. 3 is a front view of a third embodiment of the TPE device according to an embodiment of the present invention.

In a third embodiment, as can be seen in FIG. 3, the TPE device contains a withdrawal zone coincident with an infusion zone and may be called withdrawal/infusion zone -3- or venous access means. The device of the embodiment also contains a blood supply line that is made up of the means -3-, the Y-connector -36-, the tube -41-, the Y-connector -37-, the tube -42-, the pump -2-, the radial distributor -47- and the tube -43-, therefore said supply line extends from zone -3- to the inlet -4- of the separating unit -5- and transports whole blood from zone -3- to the separating unit -5-. The anticoagulant line is made up of a bag -8- of anticoagulant, a tube -45-, a Y-connector -38-, a tube -46-, a pump -7- and a Y-connector -36-, therefore said line extends from the bag -8- to the Y-connector -36-, transporting anticoagulant fluid from said bag -8- to the supply line, where it is mixed with the whole blood before said blood enters the separating unit -5-, where the blood is separated into blood plasma and formed elements. The plasma line is made up of the tube -9- and the bag -10- of plasma, said plasma line extends from the outlet -11- of the separating unit to the bag -10- and transports the blood plasma from the outlet -11- to the bag -10-, where it is stored. The line for infusion of formed elements is made up of the tube -12-, the bag -13- of formed elements, the tube -14-, the radial distributor -47-, the pump -2-, the tube -42-, the bubble detector -39-, the Y-connector -37-, the tube -41-, the Y-connector -36- and the means -3-, therefore the formed elements line extends from the outlet -16- of the separating unit to zone -3- and transports the separated formed elements from the outlet -16- to zone -3-. The line for infusion of replacement fluid is made up of the bag -20- of replacement fluid, the tube -18-, the distributor -47-, the tube -42-, the pump -2-, the detector -39-, the Y-connector -37-, the tube -41-, the Y-connector -36- and the means -3-, therefore the replacement fluid line extends from the bag -20- to zone -3-, transporting replacement fluid from said bag -20- to zone -3-. The line for therapeutic drugs is made up of the vial -32- of therapeutic drug, the tube -22-, the distributor -47-, the tube -42-, the pump -2-, the detector -39-, the Y-connector -37-, the tube -41-, the Y-connector -36- and the means -3-, therefore said line for therapeutic drugs extends from the vial -32- to zone -3-, transporting the therapeutic drug from the vial -32- to zone -3-. Moreover, the TPE device of FIG. 3 also contains means for measuring pressures of the lines, said means are made up of the tubes -40-, -41- and a unit for measuring pressures, which is not shown in the figure. Finally, the device of FIG. 3 contains the tube -44- that allows the anticoagulant line to be connected to the replacement fluid line. As mentioned above, the distributor -47- forms part of the prior art, said distributor comprises a plurality of valves that allow communication of a plurality of tubes (for example the tubes -14-, -18-, -22-, -42-, or -43-), so that by controlling said valves it is possible to allow the passage of a particular liquid and prevent the passage of other liquids through said distributor.

What is claimed is:

1. A device for therapeutic plasma exchange, comprising an extracorporeal circuit, which comprises:
   a blood line configured to receive blood from a patient,
   a separating unit configured to receive the blood from the blood line and further configured to separate the blood into formed elements and blood plasma,
   a formed elements bag configured to store at least a portion of the formed elements separated at the separating unit,
   a return line configured to receive a first flow of the formed elements and return the first flow to the patient,
   a replacement fluid line configured to infuse a plasma replacement fluid to the first flow at a first point of the return line such that the plasma replacement fluid is administered to the patient replacing the separated blood plasma,
   a drug line configured to add a therapeutic drug to the first flow at a second point of the return line such that the therapeutic drug is administered to the patient independently of administration of the plasma replacement fluid,
   an anticoagulant line for infusion of an anticoagulant,
   a conveyer to connect the replacement fluid line and the anticoagulant line,
   wherein the drug line comprises a storage of the therapeutic drug, a conveyer of therapeutic drug, a propelling device and a controller configured to control flow of the therapeutic drug, and
   wherein the drug line shares the storage, the conveyer, the propelling device, and the controller with the blood line, the return line, and the replacement fluid line, such that the device is portable; and
   a radial distributor incorporated with the controller, wherein the distributor is connected to:
   the patient's blood using the blood line;
   the formed elements bag using an infusion line for the formed elements;
   the replacement fluid bag using the replacement fluid line; and
   a vial of the therapeutic drug using the drug line;
   wherein the distributor further comprises a plurality of valves configured to control communication so as to independently control flows of the blood line, athe infusion line for the formed elements, the replacement fluid line and the drug line, and
   wherein the anticoagulant line is not connected to the radial distributor.

2. The device according to claim 1, wherein the propelling device comprises at least one peristaltic pump.

3. The device according to claim 2, wherein the at least one peristaltic pump is a reversible peristaltic pump.

4. The device according to claim 1, wherein the device has a blood withdrawal zone and a zone of infusion to the patient, which coincide.

5. The device according to claim 1, wherein the therapeutic drug comprises human plasma proteins selected from the group consisting of albumin (5-25%), α-1-antitrypsin, von Willebrand factor, clotting factors, immunoglobulins, plasminogen, plasmin, antithrombin III, fibrinogen, fibrin, thrombin and combinations thereof.

6. The device according to claim 1, wherein the separating unit is a filter.

7. The device according to claim 6, wherein the filter is a hollow-fibre filter.

8. The device according to claim 1, the replacement fluid line or the drug line comprises a bubble detector.

9. The device according to claim 1, further comprising a device configured to measure a pressure in at least one of the blood line, the return line, the replacement fluid line, and the drug line.

10. The device according to claim 1, wherein the replacement fluid is an aqueous NaCl solution with a concentration of 0.8 to 1.0% w/v.

11. The device according to claim 5, wherein the clotting factors are selected from the group consisting of factor VII, factor VIII and factor IX.

* * * * *